US00PP28299P2

(12) United States Plant Patent
Heuger

(10) Patent No.: US PP28,299 P2
(45) Date of Patent: Aug. 15, 2017

(54) ***HELLEBORUS* PLANT NAMED 'COSEH 3100'**

(50) Latin Name: *Helleborus niger*
Varietal Denomination: COSEH 3100

(71) Applicant: Josef Heuger, Glandorf (DE)

(72) Inventor: Josef Heuger, Glandorf (DE)

( * ) Notice: Subject to any disclaimer, the term of this patent is extended or adjusted under 35 U.S.C. 154(b) by 0 days.

(21) Appl. No.: 14/999,221

(22) Filed: Apr. 11, 2016

(51) Int. Cl.
*A01H 5/02* (2006.01)

(52) U.S. Cl.
USPC ..... Plt./439

(58) Field of Classification Search
USPC ..... Plt./439
See application file for complete search history.

(56) References Cited

PUBLICATIONS

UPOV hit on *Helleborus* named 'COSEH 3100', QZ PBR 20152813, published Feb. 15, 2016.*

* cited by examiner

*Primary Examiner* — Anne Grunberg
(74) *Attorney, Agent, or Firm* — C. A. Whealy

(57) ABSTRACT

A new and distinct cultivar of *Helleborus* plant named 'COSEH 3100', characterized by its relatively compact, upright and mounding plant habit; uniform and freely flowering habit; dark green-colored leaves; freely and early flowering habit; single white-colored flowers; and good garden performance.

2 Drawing Sheets

Botanical designation: *Helleborus niger.*
Cultivar denomination: 'COSEH 3100'.

BACKGROUND OF THE INVENTION

The present invention relates to a new and distinct cultivar of *Helleborus* plant, botanically known as *Helleborus niger* and hereinafter referred to by the name 'COSEH 3100'.

The new *Helleborus* plant is a product of a planned breeding program conducted by the Inventor in Glandorf, Germany. The objective of the breeding program was to create new uniform *Helleborus* plants with unique and attractive plant habit, leaf and flower coloration and resistance to pests common to *Helleborus* plants.

The new *Helleborus* plant originated from a cross-pollination conducted by the Inventor in Glandorf, Germany in November, 2008 of two unnamed proprietary seedling selections of *Helleborus niger*, not patented. The new *Helleborus* plant was discovered and selected by the Inventor as a single flowering plant from within the progeny of the stated cross-pollination grown in a controlled greenhouse environment in Glandorf, Germany in December, 2010.

Asexual reproduction of the new *Helleborus* plant by divisions in a controlled environment in Glandorf, Germany since February, 2011 has shown that the unique features of this new *Helleborus* plant are stable and reproduced true to type in successive generations.

SUMMARY OF THE INVENTION

Plants of the new *Helleborus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'COSEH 3100'. These characteristics in combination distinguish 'COSEH 3100' as a new and distinct *Helleborus* plant:

1. Relatively compact, upright and mounding plant habit.
2. Uniform and freely flowering habit.
3. Dark green-colored leaves.
4. Freely and early flowering habit.
5. Single white-colored flowers.
6. Good garden performance.

Compared to plants of the parent selections, plants of the new *Helleburus* are more uniformly mounded and are more freely flowering.

Plants of the new *Helleborus* can be compared to plants of Helleborus niger 'HGC Josef Lemper', disclosed in U.S. Plant Pat. No. 15,615. In side-by-side comparisons, plants of the new *Helleborus* differ primarily from plants of 'HGC Josef Lemper' in the following characteristics:

1. Plants of the new *Helleborus* have darker green-colored leaves than plants of 'HGC Josef Lemper'.
2. Plants of the new *Helleborus* have larger flowers than plants of plants of 'HGC Josef Lemper'.

BRIEF DESCRIPTION OF THE PHOTOGRAPHS

The accompanying colored photographs illustrate the overall appearance of the new *Helleborus* plant showing the colors as true as it is reasonably possible to obtain in colored reproductions of this type. Colors in the photographs may differ slightly from the color values cited in the detailed botanical description which accurately describe the colors of the new *Helleborus* plant.

The photograph on the first sheet is a side perspective view of a typical flowering plant of 'COSEH 3100' grown in a container.

The photograph on the second sheet is a close-up view of a typical flower of 'COSEH 3100'.

DETAILED BOTANICAL DESCRIPTION

The aforementioned photographs and following observations, measurements and values describe plants grown during the autumn in 13-cm containers in a glass-covered greenhouse in Glandorf, Germany and under cultural practices typical of commercial *Helleborus* production. During the production of the plants, day temperatures ranged from 12° C. to 32° C. and night temperatures ranged from 3° C. to 18° C. Plants were 14 months old when the photographs and the description were taken. In the following description, color references are made to The Royal Horticultural Society Colour Chart, 2015 Edition, except where general terms of ordinary dictionary significance are used.

Botanical classification: *Helleborus niger* 'COSEH 3100'.

Parentage:

*Female, or seed, parent*.—Unnamed proprietary seedling selection of *Helleborus niger*, not patented.

*Male, or pollen, parent*.—Unnamed proprietary seedling selection of *Helleborus niger*, not patented.

Propagation:

*Type*.—By tissue culture.

*Time to initiate roots, winter*.—About two months at temperatures about 12° C.

*Time to produce a rooted young plant, winter*.—About six months at temperatures ranging from 4° C. to 15° C.

*Root description*.—Thick to thin, fleshy; typically white to brown in color, actual color of the roots is dependent on substrate composition, water quality, fertilizer type and formulation, substrate temperature and physiological age of roots.

*Rooting habit*.—Sparse.

Plant description:

*Plant and growth habit*.—Herbaceous perennial; relatively compact, upright and mounding plant habit with flowers held just above the foliar plane; plant shape, roughly globular; moderately vigorous growth habit; moderate growth rate.

*Plant height, soil level to top of foliar plane*.—About 25.2 cm.

*Plant height, soil level to top of flowers*.—About 27 cm.

*Plant diameter* (*area of spread*).—About 31.6 cm.

Leaf description:

*Arrangement*.—Leaves arranged in a basal rosette; leaves palmately compound with typically seven leaflets per leaf.

*Leaf length*.—About 13 cm.

*Leaf width*.—About 13.4 cm.

*Leaflet length*.—About 9.6 cm.

*Leaflet width*.—About 3.3 cm.

*Leaf shape*.—Palmate; reniform in outline.

*Leaflet shape*.—Narrowly elliptic to narrowly obovate.

*Leaflet apex*.—Abruptly acute.

*Leaflet base*.—Attenuate.

*Leaflet margin*.—Serrate; revolute.

*Leaflet texture and luster, upper and lower surfaces*.—Smooth, glabrous; slightly rugose; glossy.

*Leaflet venation pattern*.—Pinnate.

*Leaflet color*.—Developing leaflets, upper surface: Close to NN137A. Developing leaflets, lower surface: Close to 147B. Fully developed leaflets, upper surface: Close to darker than between 147A and N189A; venation, close to 147B. Fully developed leaflets, lower surface: Close to 143A to 143B; venation, close to 144B and 183B.

*Petioles*.—Length: About 14.8 cm. Diameter: About 6 mm. Strength: Strong. Texture and luster, upper and lower surfaces: Smooth, glabrous; slightly glossy. Color, upper and lower surfaces: Close to 144B heavily tinged and speckled with close to 183B.

Flower description:

*Flower shape and habit*.—Single rotate flowers arranged solitary or in pairs; freely and uniform flowering habit with about 27 flowers developing per plant; flowers facing outwardly to slightly nodding.

*Fragrance*.—None detected.

*Natural flowering season*.—Plants begin flowering about ten months after planting; plants flower from autumn into winter in Germany.

*Flower longevity on the plant*.—About ten days; flowers not persistent.

*Flower buds*.—Length: About 2.3 cm. Diameter: About 1.2 cm. Shape: Ovate. Texture and luster: Glabrous; slightly glossy. Color: Close to NN155A; towards the base, tinged with close to 185D.

*Flower diameter*.—About 8 cm.

*Flower depth* (*height*).—About 3.5 cm.

*Petals*.—Transformed into nectaries.

*Sepals*.—Quantity and arrangement: Seven, arranged in a single whorl. Length: About 4.6 cm. Width: About 3.5 cm. Shape: Broadly ovate. Apex: Obtuse. Base: Cuneate. Margin: Entire. Texture and luster, upper surface: Glabrous; matte. Texture and luster, lower surface: Glabrous; slightly glossy. Color: When opening, upper surface: Close to NN155B. When opening, lower surface: Close to NN155B; towards the base, slightly tinged with close to 185D. Fully opened, upper surface: Close to NN155B. Fully opened, lower surface: Close to NN155D; towards the base, slightly tinged with close to 185D.

*Flower bracts*.—Quantity per flower: Typically two. Length: About 3.2 cm. Width: About 1.7 cm. Shape: Ovate. Apex: Acute. Base: Broadly cuneate. Margin: Entire; undulate. Color, upper surface: Close to 137C; venation, close to 145A. Color, lower surface: Close to 146C; venation, close to N186C.

*Peduncles*.—Length: About 20.8 cm. Diameter: About 6 mm. Aspect: About 20° from vertical. Strength: Moderately strong. Texture and luster: Glabrous; moderately glossy. Color: Close to 145B, speckled with close to 178A.

*Pedicels*.—Length: About 6.5 cm. Diameter: About 3.5 mm. Aspect: About 30° from peduncle axis. Strength: Moderately strong. Texture and luster: Glabrous; moderately glossy. Color: Close to 145B, speckled with close to 178A.

*Reproductive organs*.—Stamens: Quantity per flower: About 170. Filament length: About 1.5 cm. Filament color: Close to NN155A. Anther shape: Reniform; basifixed. Anther size: About 1.5 mm by 2 mm. Anther color: Close to 3B. Pollen amount: Moderate to abundant. Pollen color: Close to 2D. Pistils: Quantity per flower: About 7 to 20. Pistil length: About 1 cm. Stigma diameter: About 0.3 mm. Stigma shape: Club-shaped. Stigma color: Close to 150D. Style length: About 9.5 mm. Style color:

Close to NN155D. Ovary color: Close to 150D. Nectaries (transformed petals): Quantity per flower: About 15. Length: About 1.1 cm. Diameter: About 2.5 mm. Shape: Tubular, flattened. Texture and luster, inner surface: Smooth, glabrous; matte. Texture and luster, outer surface: Smooth, glabrous; glossy. Color, immature, inner and outer surfaces: Close to 150B; towards the apex, close to 150C. Color, mature, inner and outer surfaces: Close to 150B; towards the apex, close to 12A.

*Seeds and fruits*.—Seed and fruit development have not been observed on plants of the new *Helleborus*.

Garden performance: Plants of the new *Helleborus* have been observed to have good garden performance and to tolerate rain, wind and to be suitable for USDA Hardiness Zones 5 through 9.

Pathogen & pest resistance: Plants of the new *Helleborus* have not been observed to be resistant to pathogens and pests common to *Helleborus* plants.

It is claimed:

1. A new and distinct *Helleborus* plant named 'COSEH 3100' as illustrated and described.

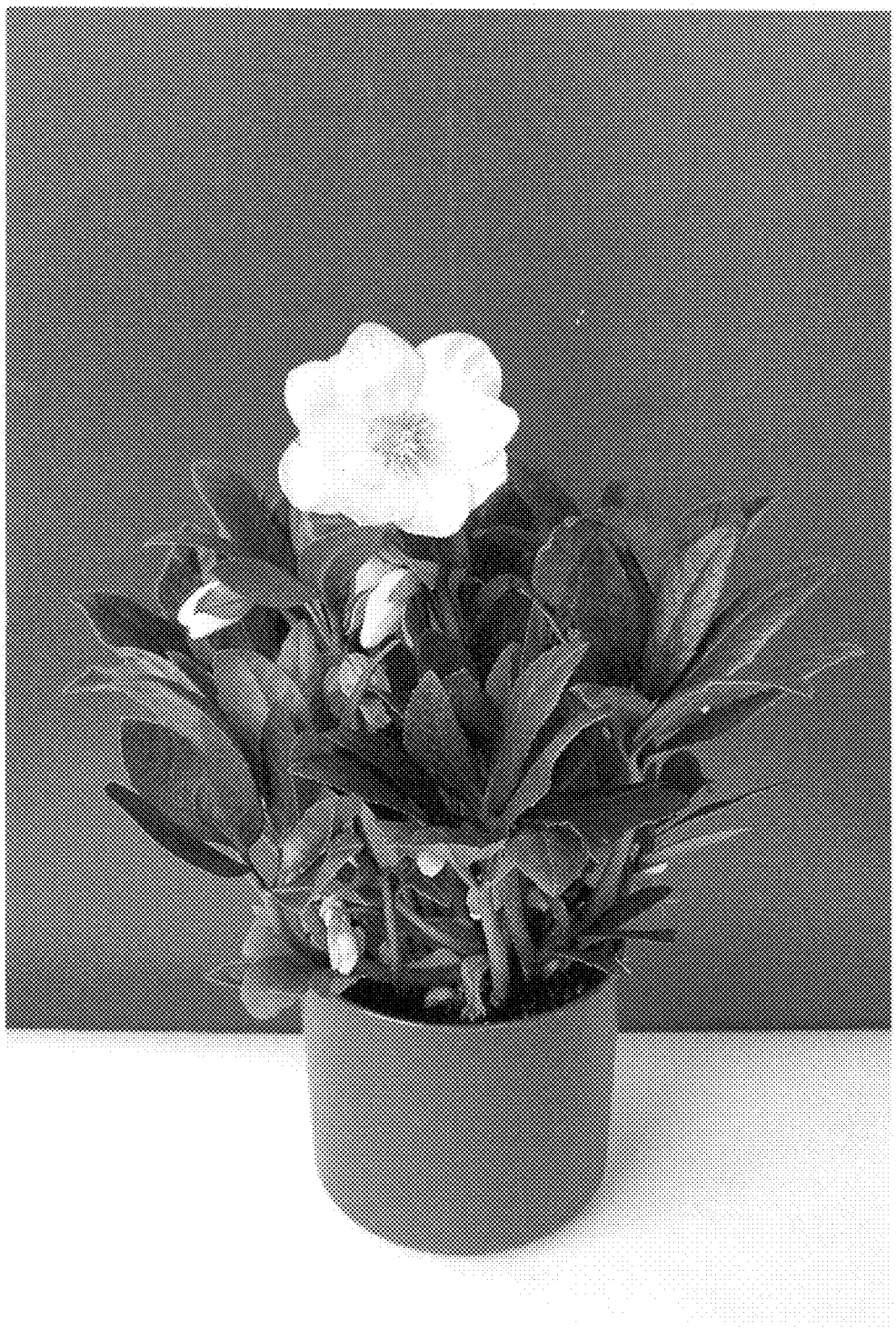

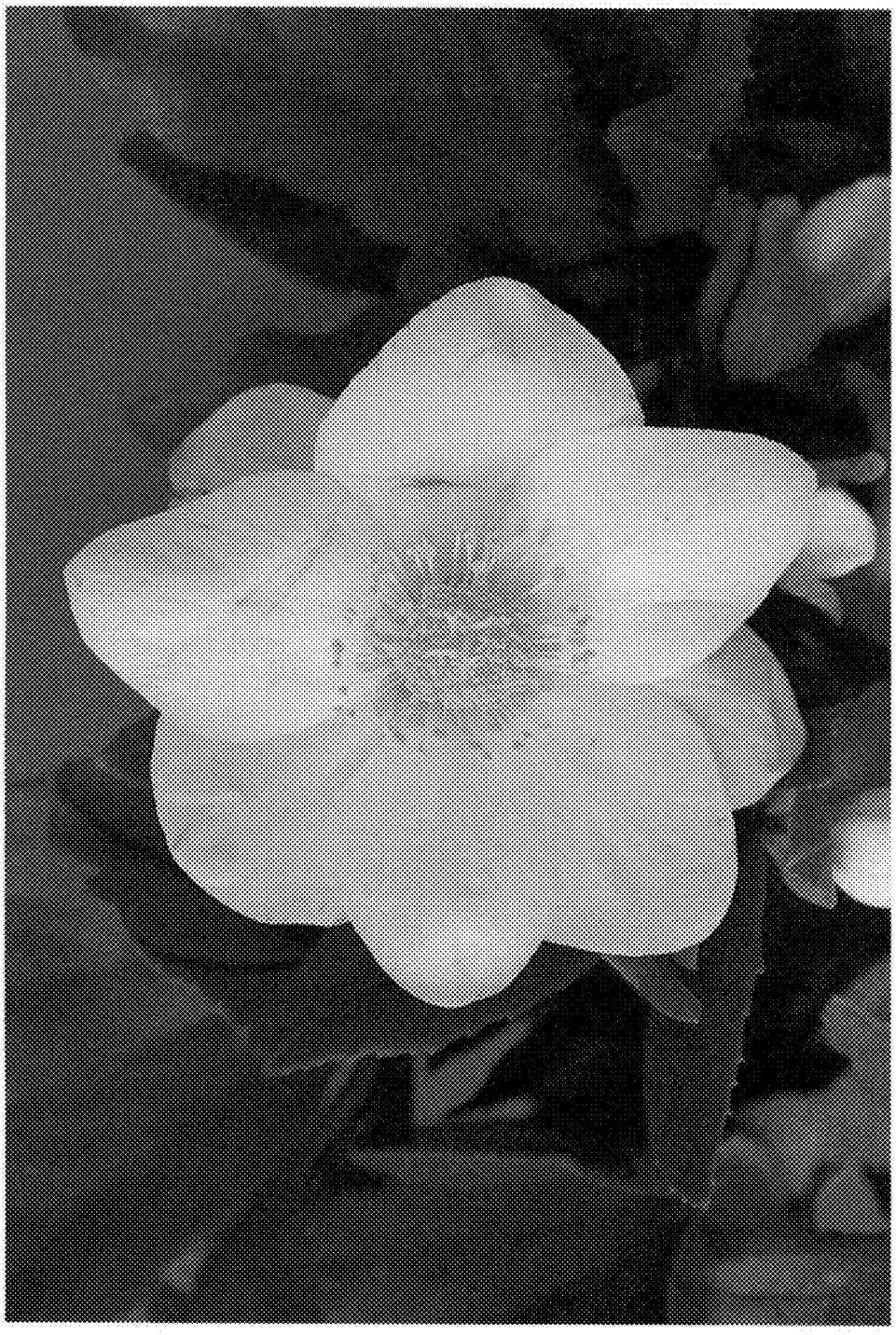

* * * * *